(12) United States Patent
Papenbrock et al.

(10) Patent No.: US 10,993,780 B2
(45) Date of Patent: May 4, 2021

(54) PROCESS WATER SUPPLY UNIT FOR SUPPLYING A MEDICAL TREATMENT UNIT, DENTAL MEDICAL TREATMENT UNIT AND OPERATING METHOD

(71) Applicant: BLUE SAFETY GMBH, Münster (DE)

(72) Inventors: Jan Papenbrock, Münster (DE);
Sebastian Fischer, Münster (DE);
Christian Mönninghoff, Münster (DE);
Mathias Maass, Hamm (DE)

(73) Assignee: BLUE SAFETY GMBH, Münster (DE)

( * ) Notice: Subject to any disclaimer, the term of this patent is extended or adjusted under 35 U.S.C. 154(b) by 20 days.

(21) Appl. No.: 15/738,704

(22) PCT Filed: Jun. 29, 2016

(86) PCT No.: PCT/EP2016/065157
§ 371 (c)(1),
(2) Date: Feb. 5, 2018

(87) PCT Pub. No.: WO2017/001486
PCT Pub. Date: Jan. 5, 2017

(65) Prior Publication Data
US 2018/0177565 A1    Jun. 28, 2018

(30) Foreign Application Priority Data
Jun. 30, 2015    (DE) .................... 10 2015 212 248.4

(51) Int. Cl.
*A61B 17/24* (2006.01)
*A61C 1/00* (2006.01)
(Continued)

(52) U.S. Cl.
CPC ............ *A61C 1/0076* (2013.01); *A61B 17/24* (2013.01); *A61C 17/02* (2013.01);
(Continued)

(58) Field of Classification Search
CPC . A61B 17/24; A61B 2217/007; A61C 1/0076; A61C 17/02; A61C 17/0217;
(Continued)

(56) References Cited

U.S. PATENT DOCUMENTS 5,120,219 A    6/1992  De Farcy
5,526,841 A    6/1996  Detsch et al.
(Continued)

FOREIGN PATENT DOCUMENTS

DE    100 59 987 A1    8/2001
EP    0 395 557 A1    10/1990
(Continued)

OTHER PUBLICATIONS

English Language Translation of 10-0585493B1 to Kim (2006) (obtained from Google Patents Jul. 2019) (Year: 2006).*

(Continued)

*Primary Examiner* — Lucas A Stelling
(74) *Attorney, Agent, or Firm* — Norris McLaughlin, P.A.

(57) ABSTRACT

Process water supply unit for supplying a medical treatment unit with process water (BW), containing biocide, comprising: a container receptacle for receiving a pressurised water container; a compressed air inlet for connecting the process water supply unit to a compressed-air source; a compressed-air connection, via which compressed air (DL) originating from the compressed-air inlet can be introduced into the pressurised water container; and a process water connection, via which the process water (BW) which is to be delivered out from the pressurised water container by the compressed air (DL) introduced into the pressurised water container can (Continued)

be dispensed to the medical treatment unit, wherein the process water supply unit has a sterile air filter which is integrated into a compressed-air path between the compressed-air inlet and the compressed-air connection or into a compressed-air path between the external compressed-air source and the compressed-air connection.

7 Claims, 9 Drawing Sheets

(51) Int. Cl.
| | |
|---|---|
| A61C 17/02 | (2006.01) |
| A61L 9/16 | (2006.01) |
| B01D 46/00 | (2006.01) |
| C02F 1/00 | (2006.01) |
| C02F 1/50 | (2006.01) |
| C02F 103/00 | (2006.01) |

(52) U.S. Cl.
CPC ............ *A61C 17/0217* (2013.01); *A61L 9/16* (2013.01); *B01D 46/0027* (2013.01); *C02F 1/001* (2013.01); *C02F 1/50* (2013.01); *A61B 2217/007* (2013.01); *A61L 2209/14* (2013.01); *B01D 2279/65* (2013.01); *C02F 2103/006* (2013.01); *C02F 2303/04* (2013.01)

(58) Field of Classification Search
CPC ... A61C 17/024; A61C 17/028; A61C 17/032; A61L 9/16; A61L 2209/14; B01D 46/0027; B01D 46/0028; B01D 46/0038; B01D 2279/65; B01D 2221/10; C02F 1/001; C02F 1/50; C02F 1/68; C02F 1/686; C02F 1/685

See application file for complete search history.

(56) References Cited

U.S. PATENT DOCUMENTS

| | | | |
|---|---|---|---|
| 6,107,097 A | | 8/2000 | Pfeifer |
| 2003/0036033 A1* | | 2/2003 | Chandler ............ A61C 1/0061 |
| | | | 433/77 |
| 2004/0202980 A1* | | 10/2004 | Policicchio ............ A61C 3/025 |
| | | | 433/88 |
| 2012/0282568 A1* | | 11/2012 | Disel ...................... A61C 17/02 |
| | | | 433/80 |

FOREIGN PATENT DOCUMENTS

| | | |
|---|---|---|
| EP | 0 886 778 B1 | 12/1998 |
| EP | 1 468 659 A2 | 10/2004 |
| JP | H03-012146 A | 1/1991 |
| JP | H07-116182 A | 5/1995 |
| JP | H 11 104149 A | 4/1999 |
| KR | 100585493 B1 * | 5/2006 |
| KR | 100585493 B1 | 5/2006 |
| RU | 2 174 385 C1 | 10/2001 |
| WO | 2009 016655 A1 | 2/2009 |

OTHER PUBLICATIONS

German Search Report for corresponding to German Application No. 10 2015 219659.3 dated Apr. 29, 2016.
English translation of Office Action, dated Jun. 30, 2020, issued in connection with Japanese Application No. 2017-568452.

* cited by examiner

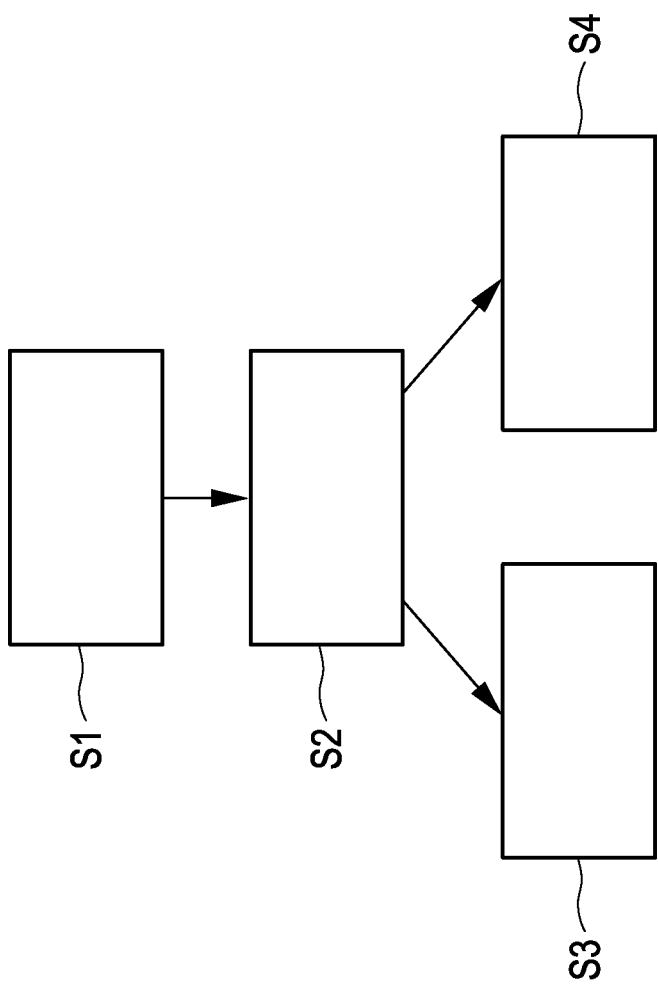

PROCESS WATER SUPPLY UNIT FOR SUPPLYING A MEDICAL TREATMENT UNIT, DENTAL MEDICAL TREATMENT UNIT AND OPERATING METHOD

This application is the U.S. National Stage of International Application No. PCT/EP2016/065157, filed Jun. 29, 2016, which claims foreign priority benefit under 35 U.S.C. § 119 of German Application No. 10 2015 212 248.4 filed Jun. 30, 2015.

The present invention relates to a process water supply unit and an operating method for supplying a medical treatment unit with process water, preferably containing biocide. The present invention additionally relates to a dental medical treatment unit. The dental medical treatment unit can be a rotating instrument in the form of a drill or can have such a drill. The process water is typically used to cool the instrument and to rinse a patient's oral cavity.

Process water supply units of the prior art have a container receptacle for receiving a pressurized water container and a compressed-air inlet for connecting the process water supply unit to an external compressed-air source, for example a compressed-air compressor in a dental medical practice. In addition, a compressed-air connection is provided, via which compressed air originating from the compressed-air inlet can be introduced into the pressurized water container. Furthermore, known process water supply units have a process water connection, via which the process water which is to be delivered out from the pressurized water container by the compressed air introduced into the pressurized water container can be dispensed to the dental medical treatment unit.

It is the object of the present invention to indicate a process water supply unit, a dental medical treatment unit as well as an operating method which are particularly safe and inexpensive.

With regard to the process water supply unit, the object is achieved in that the process water supply unit has a sterile air filter which is integrated into a compressed-air path between the compressed-air inlet and the compressed-air connection or into a compressed-air path between the external compressed-air source and the compressed-air inlet.

The invention includes the realization that compressed air is typically produced in dental practices by central compressed-air compressors. There is therefore a risk that dirt particles and microorganisms located therein are sucked in and supplied via a system of compressed-air lines to a treatment unit and therefore to the patient. To avoid this disadvantage, compressors having integrated air filters have been proposed in the prior art.

Departing from this, the process water supply unit according to the invention has a sterile air filter. Therefore, protection against infection can be advantageously provided directly at the treatment site. Any damage to the system of compressed-air lines and/or to the compressor, or improper maintenance of the same can be effectively compensated for. The process water supply unit according to the invention is therefore particularly safe.

In one preferred configuration, the sterile air filter has a pore size of <90 μm (micrometers). It has proven to be advantageous if the pore size is <50 μm, particularly preferably <10 μm. In one particularly preferred configuration, the sterile air filter has a pore size of <0.2 μm.

In order to provide a particularly compact process water supply unit, it has proven to be advantageous if the sterile air filter is arranged inside a housing volume of the process water supply unit. The sterile air filter is particularly preferably integrated into the compressed-air path between the compressed-air inlet and the compressed-air connection. Alternatively, the sterile air filter can be arranged outside a housing volume of the process water supply unit. The sterile air filter is then preferably arranged on or near a housing volume or respectively a housing of the process water supply unit.

If the sterile air filter is integrated into the compressed-air path between the external compressed-air source and the compressed-air connection, the sterile air filter is preferably arranged at the end with respect to a compressed-air hose which connects the external compressed-air source to the compressed-air connection of the process water supply unit.

A compressed-air path between the external compressed-air source, i.e. for example a compressor, and the sterile air filter is preferably equipped without additional filter elements, i.e. is filter-free. As an alternative to arranging the sterile air filter directly at the end in the compressed-air path between the external compressed-air source and the compressed-air connection, the sterile air filter can be arranged in the vicinity of the compressed-air connection.

The length of a compressed-air line between a sterile air filter arranged outside the process water supply unit and the compressed-air connection on or in the housing of the process water supply unit is preferably <5 m, preferably <2 m, more preferably <1 m.

In one preferred configuration, the process water supply unit has a switch, by means of which the compressed-air path between the compressed-air inlet and the compressed-air connection can be interrupted and/or released. The switch is preferably downstream, preferably immediately downstream, of the sterile air filter. Alternatively, the switch can be upstream of the sterile air filter.

The process water supply unit can have a cylindrical lid part. The cylindrical lid part preferably surrounds the sterile air filter, preferably completely. The process water supply unit can have a plate-shaped base plate. The plate-shaped base plate can at least partially form the container receptacle for receiving the pressurized water container. The process water connection and the compressed-air connection can run at least in sections through the plate-shaped base plate.

It has proven to be advantageous if the plate-shaped base plate has a circumferential seal or a circumferential seal is assigned to the plate-shaped base plate. The circumferential seal can seal the pressurized water container from the surroundings if it is fastened to the container receptacle. The circumferential seal is preferably a sealing ring.

In one particularly preferred configuration, the plate-shaped base plate is arranged completely inside the cylindrical lid part. This results in a particularly compact and easy to clean construction of the process water supply unit.

The cylindrical lid part can have, on its inner circumference, at least one latching element, into which a corresponding latching element of the pressurized water container can engage in order to hold the pressurized water container on the container receptacle. The latching element is preferably configured as a ramp or respectively in the form of a ramp on the inner circumference of the cylindrical lid part. Multiple latching elements can be arranged, preferably uniformly spaced from one another, on the inner circumference of the cylindrical lid part. Three latching elements in the form of a ramp are preferably arranged on the inner circumference of the cylindrical lid part.

It has proven to be advantageous if the pressurized water container which is, for its part, preferably configured in the form of a cylinder, has on its outer circumference at least one corresponding latching element. The corresponding latching element is preferably a latching nose which is configured to engage in a latching element in the form of a ramp on the inner circumference of the cylindrical lid part. Multiple, preferably three corresponding, latching elements can be provided on sides of the pressurized water container.

In another preferred configuration, the process water supply unit has a sterile water filter. The sterile water filter can be (preferably immediately) upstream or downstream of the process water connection. In one preferred configuration, the sterile water filter has a pore size of <90 μm (micrometers). It has proven to be advantageous if the pore size is <50 μm, particularly preferably <10 μm. In one particularly preferred configuration, the sterile water filter has a pore size of <0.2 μm.

The sterile water filter is particularly preferably arranged in the process water supply unit at the end with respect to a process water path. Biocide-free process water provided in the process water supply unit can be effectively sterilized by means of a provided sterile water filter as it emerges from the process water supply unit. The sterile water filter can of course also be provided in the event that process water containing biocide is used.

In one particularly preferred configuration, the pressurized water container for storing the process water is encompassed by the process water supply unit. It has proven to be advantageous if the pressurized water container has a volume between 100 ml and 5000 ml (milliliters). The volume of the pressurized water container can be between 1000 ml and 2000 ml, preferably between 1000 ml and 1300 ml. The pressurized water container is preferably configured in the form of a cylinder. The pressurized water container is particularly preferably pressure-resistant up to at least 3 bar, preferably 5 bar. The pressurized water container can preferably be autoclaved. The pressurized water container can consist of, for example, plastic or metal.

The object is also achieved by a dental medical treatment unit having a previously described process water supply unit. Equally, the object is achieved by using a previously described process water supply unit in a dental medical treatment unit.

The object is also achieved by an ENT (ear, nose, throat) treatment unit having a previously described process water supply unit as well as by using a process water supply unit of the previously described type in an ENT treatment unit.

In one preferred configuration of the dental medical treatment unit (dental unit), the process water connection of the process water supply unit is connected to a process water intake of the dental medical treatment unit. The process water can be supplied to a rinsing head or a drill of the dental medical treatment unit via the process water intake of the dental medical treatment unit.

In another preferred configuration, the compressed-air inlet of the process water supply unit is connected to a compressed-air outlet of the dental medical treatment unit. The dental medical treatment unit can itself have a compressor or similar as a compressed-air source or can be supplied, for its part, via a compressor or a central compressed-air system.

In the case of the dental medical treatment unit, a sterile air filter is also preferably arranged inside a housing of the encompassing process water supply unit. Alternatively or in addition, the sterile air filter can be arranged outside the housing of the process water supply unit and in the compressed-air path, more precisely in the compressed-air hose, between the compressed-air outlet of the dental medical treatment unit and the compressed-air inlet of the process water supply unit.

The ENT treatment unit according to the invention having the process water supply unit can be further developed in accordance with the dental medical treatment unit.

According to another aspect of the invention, the object is achieved by a method for operating a process water supply unit, in particular a previously described process water supply unit, having the following steps:

guiding in particular unfiltered compressed air from the compressed-air source to the sterile air filter of the process water supply unit;

introducing the compressed air filtered by the sterile air filter of the process water supply unit into a pressurized water container;

wherein the pressurized water container is filled with process water, preferably containing biocide, during a treatment, so that the process water is dispensed via a process water connection of the process water supply unit; and/or wherein the pressurized water container is substantially free of process water during a cleaning phase, so that an air path downstream of the sterile air filter is cleared by blowing by means of the compressed air filtered by the sterile air filter.

As a result of the method according to the invention, the process water can, on the one hand, be discharged from the pressurized water container by substantially germ-free compressed air. On the other hand, a dental medical treatment unit downstream of the process water supply unit can be cleared by blowing with sterile compressed air in a cleaning phase. To this end, the pressurized water container is fastened to the process water supply unit emptied or respectively free of process water and is acted on with compressed air. Sterile compressed air then travels into a path downstream of the process water connection via the process water connection which is connected to the dental medical treatment unit, via which process water is guided during the treatment operation. A dental medical treatment unit or an ENT treatment unit can be advantageously blown dry with sterile air. This is desirable, for example, overnight or at weekends, in order to exclude the possibility of process water stagnating during these periods in the components or hoses of the ENT treatment unit or dental medical treatment unit which otherwise carry water. This can prevent an undesired colonization with biofilms. The sterile air, which is produced by means of the sterile air filter, therefore effectively prevents the respective treatment units from being contaminated by means of microorganisms and nutrients which are typically brought in via unfiltered compressed air.

The method according to the invention can be further developed by features which are described with reference to the process water supply unit and/or the medical treatment unit.

Embodiment examples of the invention will now be described below with the aid of the drawings. Further advantages, features and details of the invention are set out by the following description of the preferred embodiment examples as well as with the aid of the drawings; wherein:

FIG. 9 shows a schematic representation of a method for operating a process water supply unit according to the invention.

Figure 1:
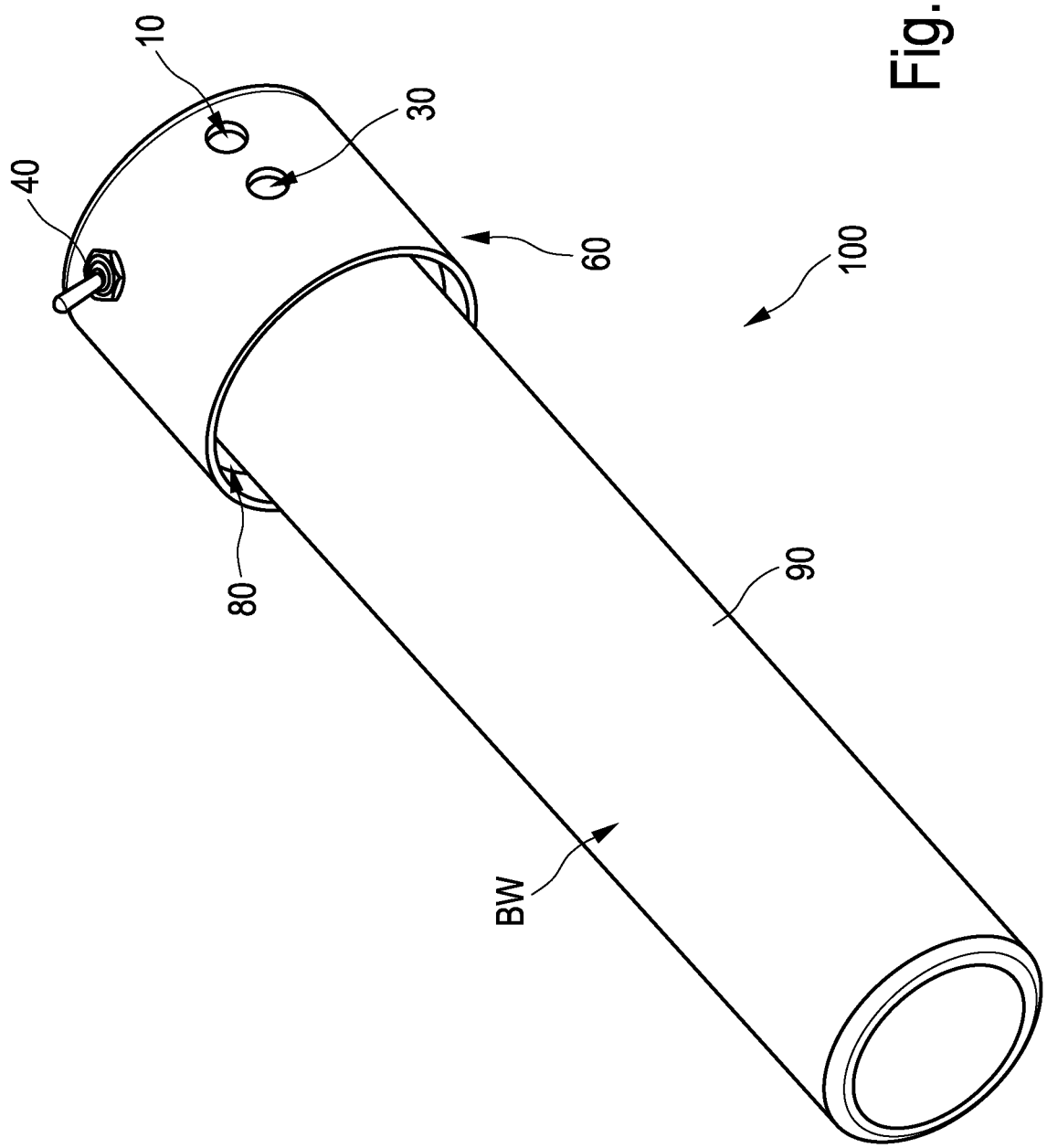
FIG. 1 shows a schematic representation of an embodiment example of a process water supply unit according to the invention.

A process water supply unit 100 is shown in FIG. 1. The process water supply unit 100 has a cylindrical lid part 60. A compressed-air inlet 10 for connecting the process water supply unit 100 to a compressed-air source 300 is arranged on the lid part 60 (cf. FIG. 7). In addition, a process water connection 30 is provided on the cylindrical lid part 60, via which process water connection process water can be dispensed to a medical treatment unit 200 (cf. FIG. 7).

The process water supply unit 100 has a container receptacle 80, on which, in the embodiment example shown here, a pressurized water container 90 configured in the form of a cylinder is arranged. Process water BW containing biocide which is to be dispensed via the process water connection 30 is filled in the pressurized water container 90. Compressed air at the compressed-air inlet 10 can be released via a switch 40 provided in the cylindrical lid part 60, and the process water BW provided in the process water container 90 can be conducted out of the process water connection 30 by means of compressed air DL.

Figure 2:
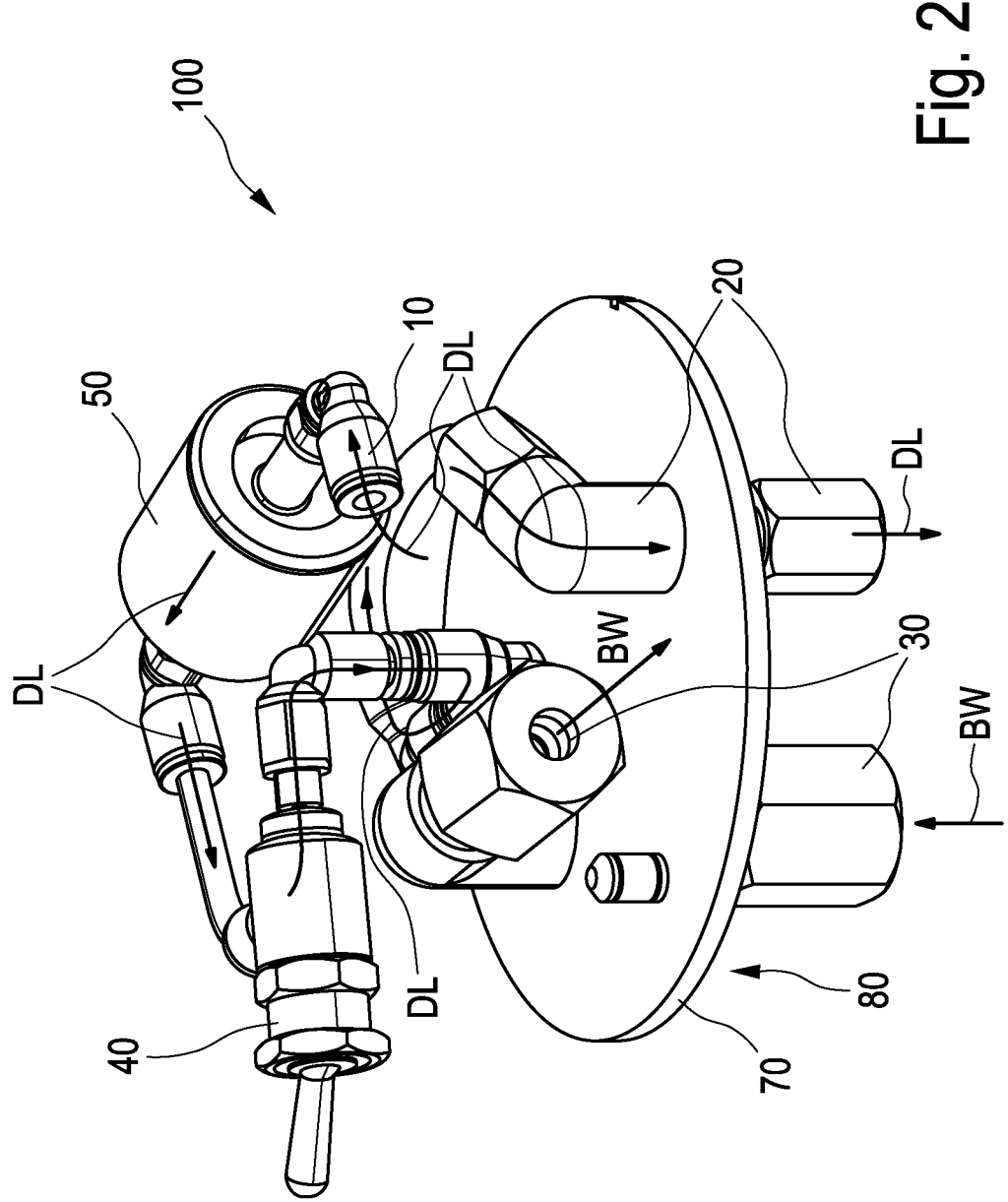
FIG. 2 shows a schematic representation of an inner view of the process water-supply unit from FIG. 1.

FIG. 2 shows the inner view of the process water supply unit 100 of FIG. 1. For reasons of clarity, the cylindrical lid part 60 (cf. FIG. 1) has not been shown. The process water supply unit of FIG. 1 comprises the compressed-air inlet 10, via which compressed air DL can flow into a sterile air filter 50 encompassed by the process water supply unit 100. The sterile air filter 50 is arranged, in the embodiment example shown here, inside a housing volume, or more accurately, inside a volume of the cylindrical lid part 60 (cf. FIG. 1).

The process water supply unit 100 additionally has a compressed-air connection 20, via which compressed air DL originating from the compressed-air inlet 10 can flow. In the embodiment example shown here, the process water supply unit 100 has a plate-shaped base plate 70. The compressed-air connection 20 runs at least in sections through the base plate. Likewise, the process water supply unit 100 has a process water connection 30 which, as shown, runs in sections through the plate-shaped base plate 70.

A container receptacle 80 for receiving a pressurized water container (cf. FIG. 1) is formed here by the plate-shaped base plate 70. This means the process water connection 30 protruding on the lower side of the plate-shaped base plate 70 as well as the compressed-air connection 20 protruding on the lower side of the plate-shaped base plate 70 project into a volume of the pressurized water container 90, if the latter is arranged on the container receptacle 80.

As can be inferred from FIG. 2, the sterile air filter 50 is immediately downstream of the compressed-air inlet 10. Located in turn immediately downstream of the sterile air filter 50 is a switch 40, by means of which the compressed-air path between the compressed-air inlet 10 and the compressed-air connection 20 can be interrupted and released.

The function of the process water supply unit 100 according to the invention will be explained in more detail below. Compressed air DL originating from a compressed-air source enters the compressed-air inlet 10 in the direction of the arrow. The compressed air DL entering the compressed-air inlet 10 is substantially unfiltered, i.e. it can still contain germs. During the further course of the compressed-air path, the compressed air DL travels through the sterile air filter 50 which has a pore size of <0.2 μm in this case.

The compressed air DL continues to travels via a hose connection to the switch 40 which, in the embodiment example shown here, is shown in the open position. Accordingly, the compressed air DL can continue to flow, unhindered, in the direction of the compressed-air connection 20, in order to travel via the latter into the pressurized water container 90 (cf. FIG. 1).

Process water BW is pressed by means of the compressed air DL introduced into the pressurized water container 90 into the process water connection 30 on the lower side of the plate-shaped base plate 70 in the direction of the arrow according to the displacement principle, in order to emerge from the process water connection on the part of the process water connection 30 located above the plate-shaped base plate 70. A process water supply line 230 leading to a dental medical treatment unit 200 is typically connected to the part of the process water connection 30 located on the upper side of the plate-shaped base plate 70 (cf. FIG. 7).

It is noted that the inlet of the compressed-air inlet 10 is not, as shown in FIG. 1, necessarily arranged on the cylindrical lid part 60. Rather, the cylindrical lid part 60 can also have a through-opening, via which a compressed-air hose which is intended to connect to the compressed-air inlet 10 is to be guided through. The same applies accordingly to the process water connection.

Figure 3:
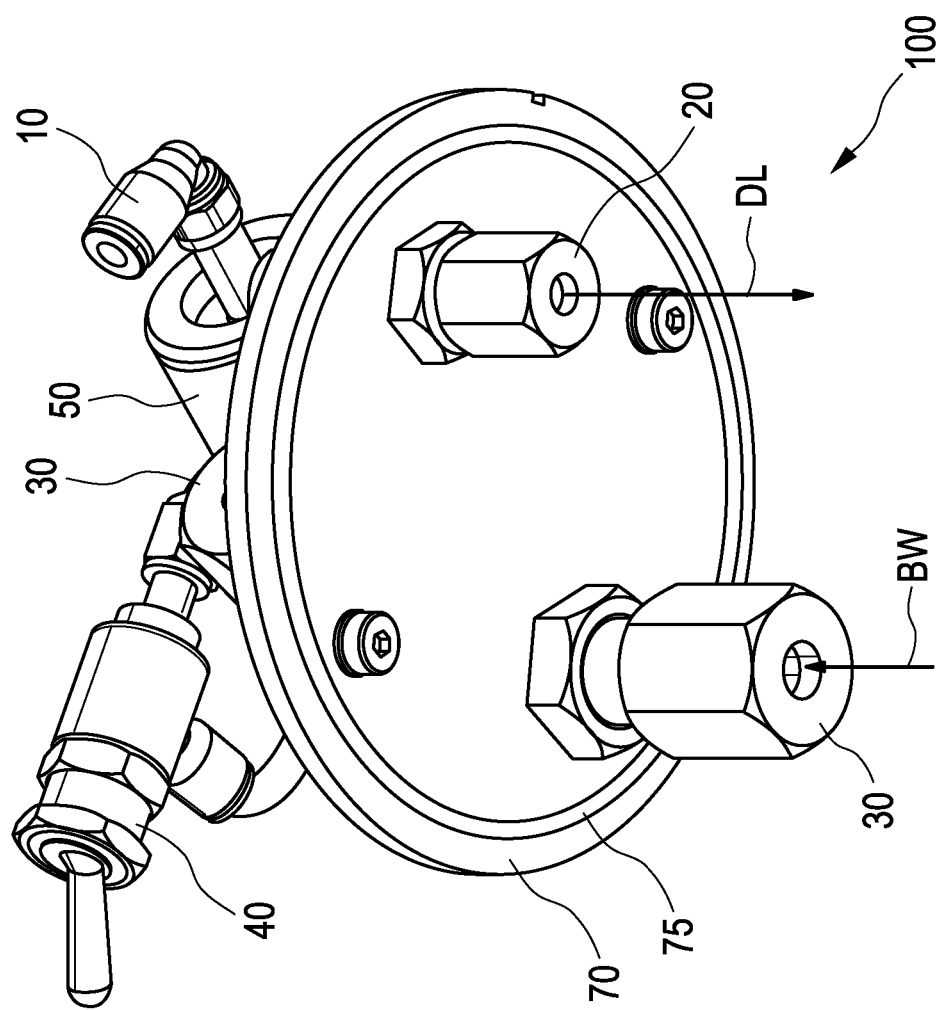
FIG. 3 shows a bottom view of the representation from FIG. 2.

FIG. 3 shows the process water supply unit 100 of FIG. 2 in a bottom view, i.e. looking from the direction of the pressurized water container 90. Clearly visible on the lower side of the plate-shaped base plate 70 are the sections of the compressed-air connection 20 or respectively of the process water connection 30 projecting into the pressurized water container 90 (if assembled). The flow direction of the compressed air DL and the flow direction of the process water BW are marked by the direction of the arrow.

The plate-shaped base plate 70 has, on its underside, a circumferential seal 75, in this case a sealing ring. A pressurized water container 90, if the latter as shown in FIG. 1 is arranged in the cylindrical lid part 60, is sealed from the surroundings by the circumferential seal 75.

Figure 4:
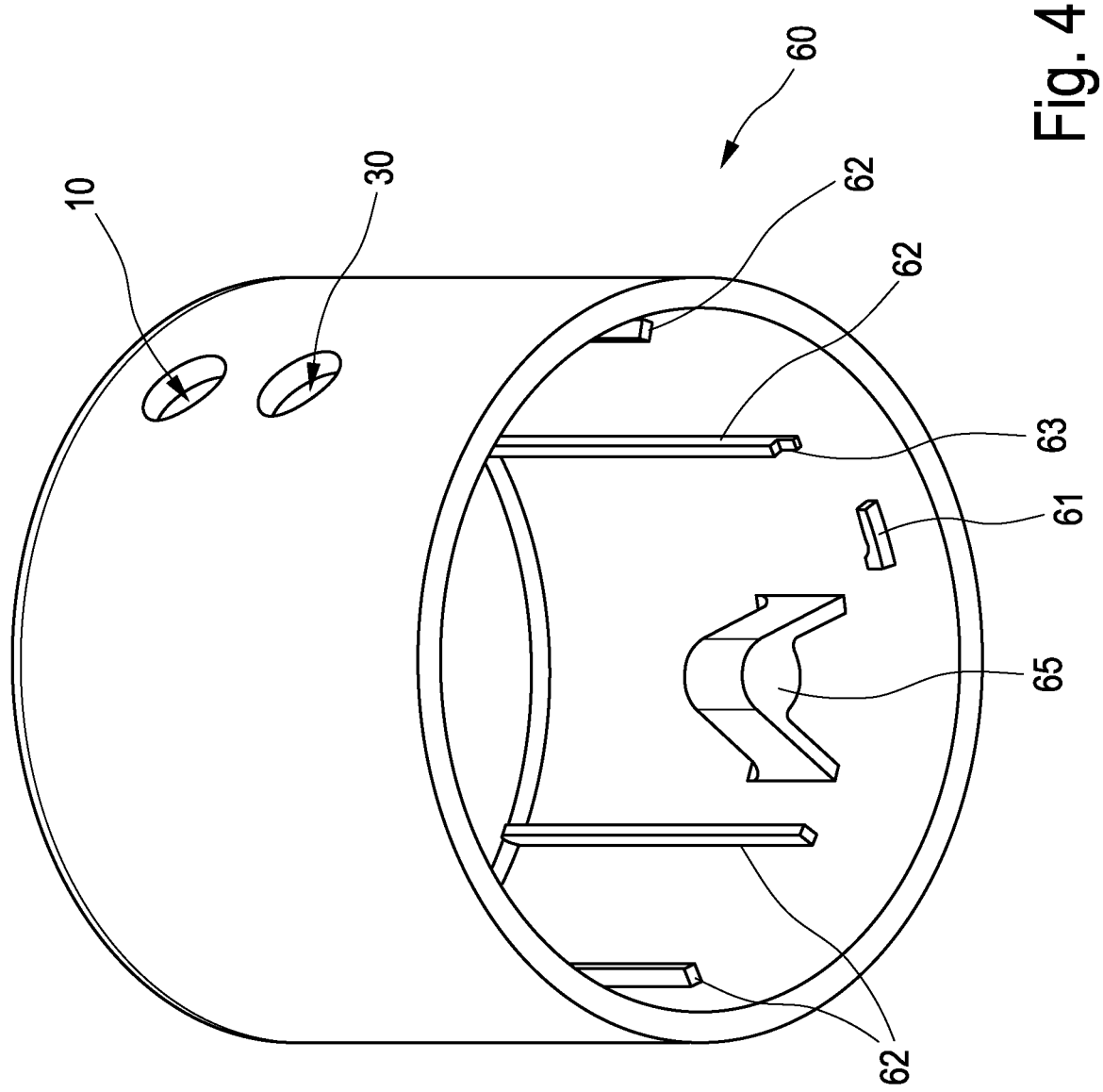
FIG. 4 shows a schematic representation of a cylindrical lid part of the process water supply unit from FIG. 1.

FIG. 4 then shows the cylindrical lid part 60 in a bottom view. Openings for guiding through the connection hoses leading to the compressed-air inlet 10 or respectively process connection 30 are indicated in the upper part of the cylindrical lid part 60.

Webs 62 oriented axially to the cylindrical lid part 60, which serve to support the plate-shaped base plate 70 (cf. FIG. 5), extend on the inner circumference of the cylindrical lid part. One of the webs 62 has a recess 63 on the lower side, which make it possible to insert the plate-shaped base plate 70 into the cylindrical lid part 60 in the correct rotational position. A bridge 65 which is also provided on the inner side of the cylindrical lid part 60 serves to screw the plate-shaped base plate 70 to the cylindrical lid part 60.

In order to be able to hold a pressurized water container in the cylindrical lid part 60, a latching element 61 in the form of a ramp is arranged on the inner circumference of the cylindrical lid part 60. This will be explained more precisely below with reference to FIG. 6.

Figure 5:
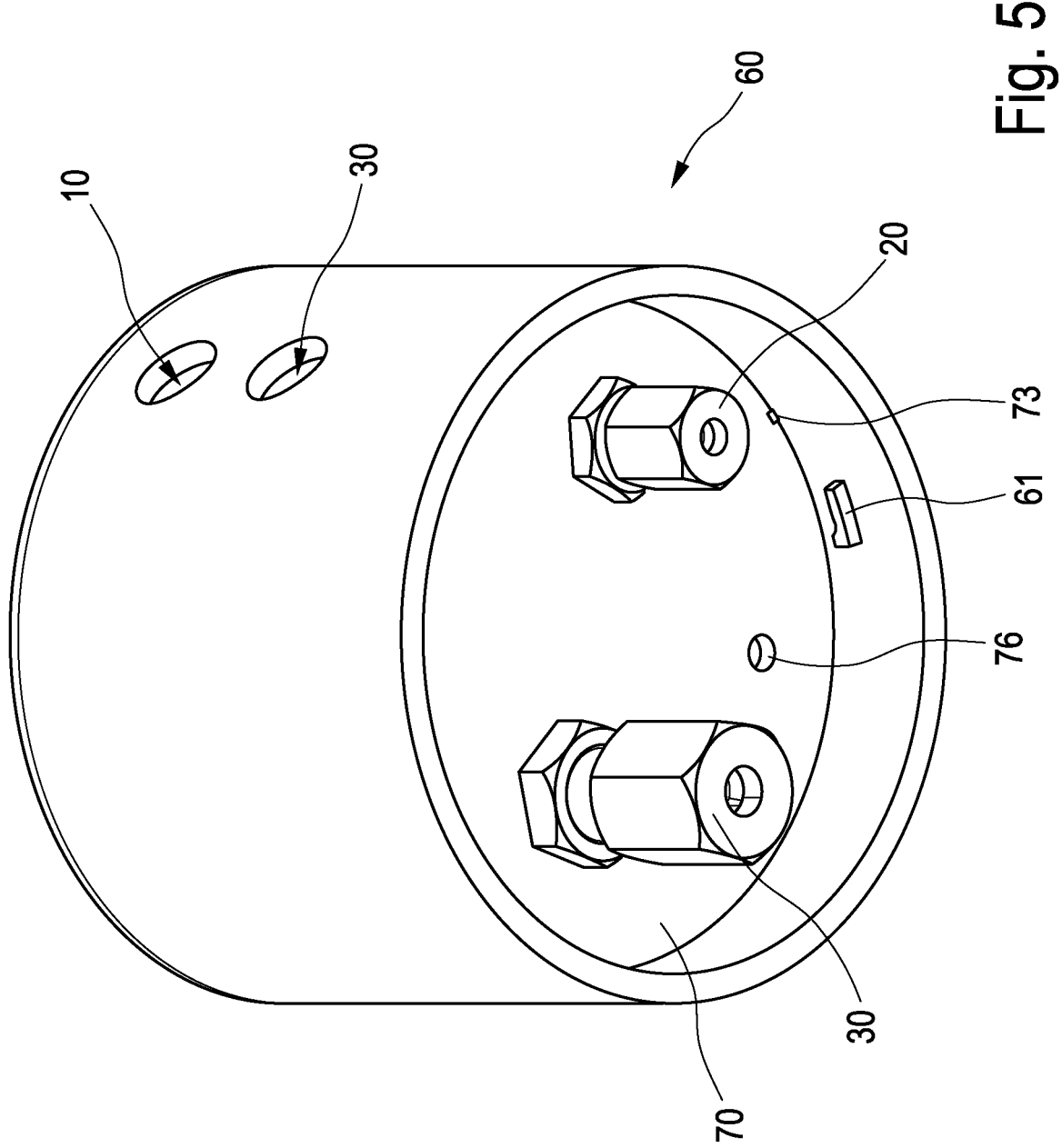
FIG. 5 shows the cylindrical lid part of FIG. 4 with the base plate inserted.

FIG. 5 then shows the cylindrical lid part 60 of FIG. 4 with an inserted plate-shaped base plate 70. The plate-shaped base plate 70 has a through-opening 76, via which the plate-shaped base plate 70 can be screwed to the web 65 (cf. FIG. 4) of the cylindrical lid part 60. As can be inferred from FIG. 5, the plate-shaped base plate 70 is arranged completely inside the cylindrical lid part 60. The sterile air filter (not shown here), which is located on the upper side of the plate-shaped base plate 70, is likewise arranged completely inside the cylindrical lid part 60. A corresponding recess 73 on the plate-shaped base plate 70 interacting with the recess 63 on the lower side (cf. FIG. 4) serves to insert the plate-shaped base plate 70 into the cylindrical lid part 60 in the correct rotational position.

Figure 6:
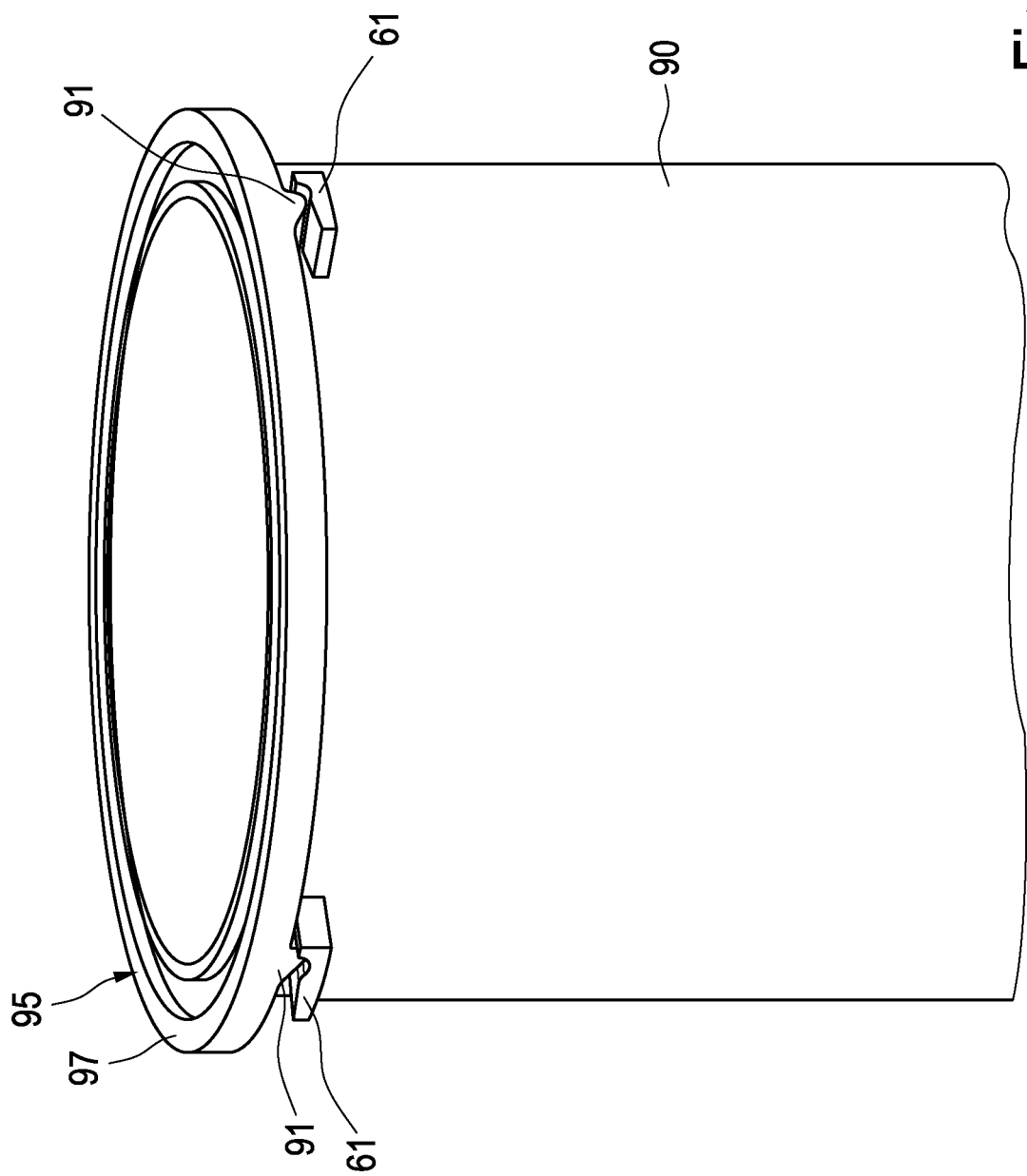
FIG. 6 shows a perspective representation of a pressurized water container of the process water supply unit of FIG. 1.

The fastening of the pressurized water container 90 is to now be explained more precisely with reference to FIG. 6. For representation reasons, the cylindrical lid part 60 (cf. FIGS. 1 and 5) is not shown in FIG. 6. Rather, only two latching elements 61 of the lid part are arranged as parts of the cylindrical lid part in FIG. 6.

In total, three latching elements 61 are provided on the circumference side, only two of which are visible in FIG. 6. The latching elements 61 of the cylindrical lid part in this case are configured in the form of a ramp. The pressurized water container 90, which is configured in the form of a cylinder in the embodiment example shown here, has an annular collar 97 which is intended to rest on the plate-shaped base plate 70 (cf. FIG. 5). Latching elements 91 in the form of latching noses are arranged on the collar 97, which correspond to the latching elements 61 of the cylindrical lid part, which are configured in the form of a ramp.

In order to arrange the pressurized water container 90 on the container receptacle of the process water supply unit 100, the pressurized water container 90 is held coaxially to the cylindrical lid part 60 and pushed into the cylindrical lid part 60. By means of a slight rotational movement, in this case in the clockwise direction, the corresponding latching elements 91 of the pressurized water container 90 can be brought into a latching connection with the latching elements 61 of the cylindrical lid part. In the embodiment example shown here, a rotation of less than 20° is required in order to engage the pressurized water container 90 in the cylindrical lid part 60. Consequently, the pressurized water container 90 can be advantageously replaced particularly quickly.

In order to guarantee sealing between the pressurized water container 90 and the plate-shaped pressure plate 70, a circumferential groove 95 is configured on the collar 97 of the pressurized water container 90, into which a circumferential seal 75 (cf. FIG. 3) can engage. The circumferential seal 75 is not necessarily arranged on the plate-shaped base plate 70. Rather, the circumferential seal 75 can also be provided as a separate sealing ring.

Figure 7:
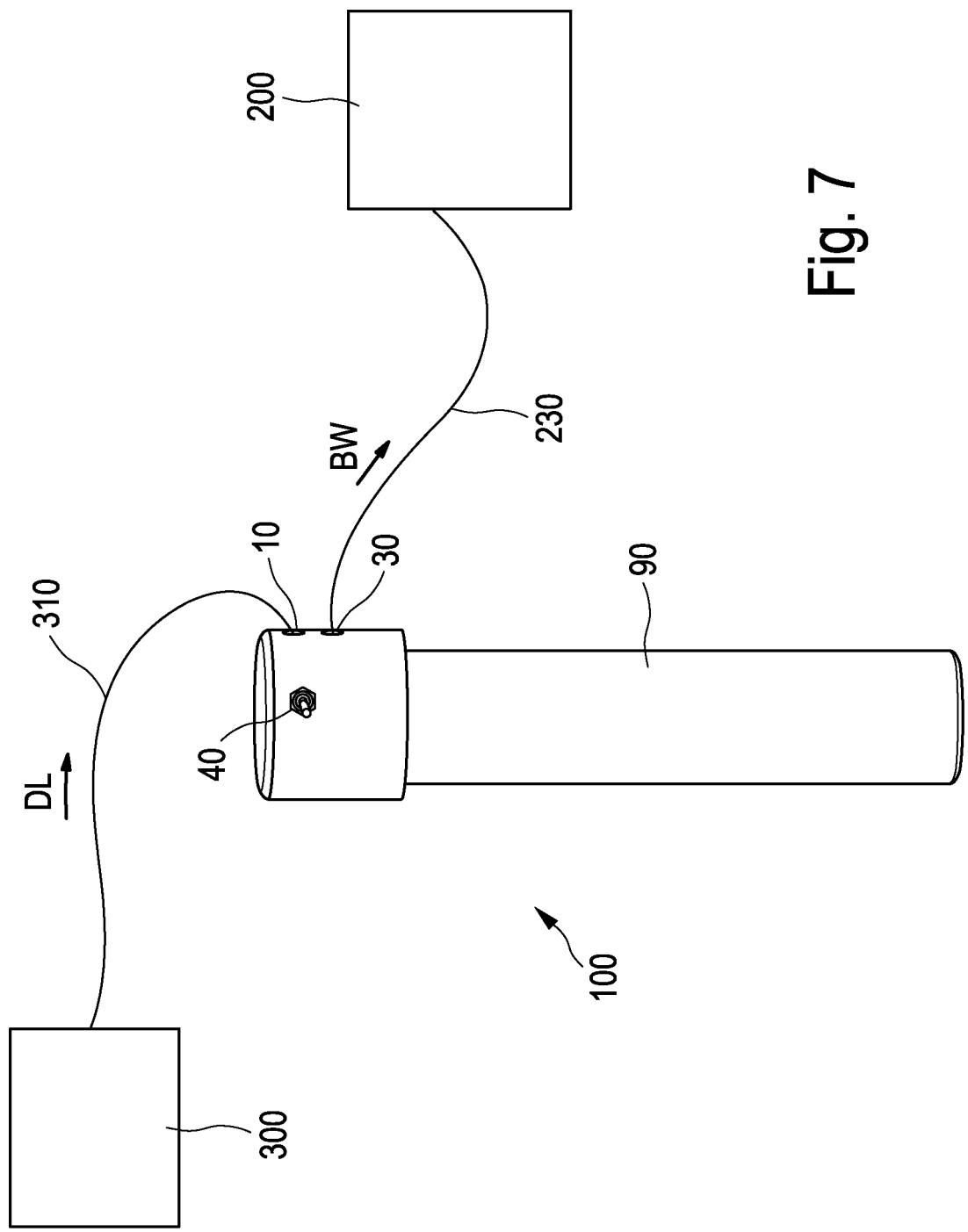
FIG. 7 shows a first embodiment example of a dental medical treatment unit having a process supply unit.

FIG. 7 shows a process water supply unit 100 according to the invention, which is connected to a dental medical treatment unit 200 and a compressed-air source 300. A compressed-air source 300 in the form of a compressor is connected via a compressed-air supply line 310 to the compressed-air inlet 10 of the process water supply unit 100, so that compressed air DL originating from the compressed-air source 300 can flow into the compressed-air inlet 10.

As a result of the introduced compressed air DL, process water BW located in the pressurized water container 90 is supplied via a process water supply line 230 to the medical treatment unit 200, in this case to a dental unit. In the medical treatment unit 200 which is provided as a dental unit, the process water BW is in turn supplied to a drill or a rinsing head. In the embodiment example shown in FIG. 7, the sterile air filter 50 provided according to the invention is arranged inside a housing of the process water supply unit 100.

Figure 8:
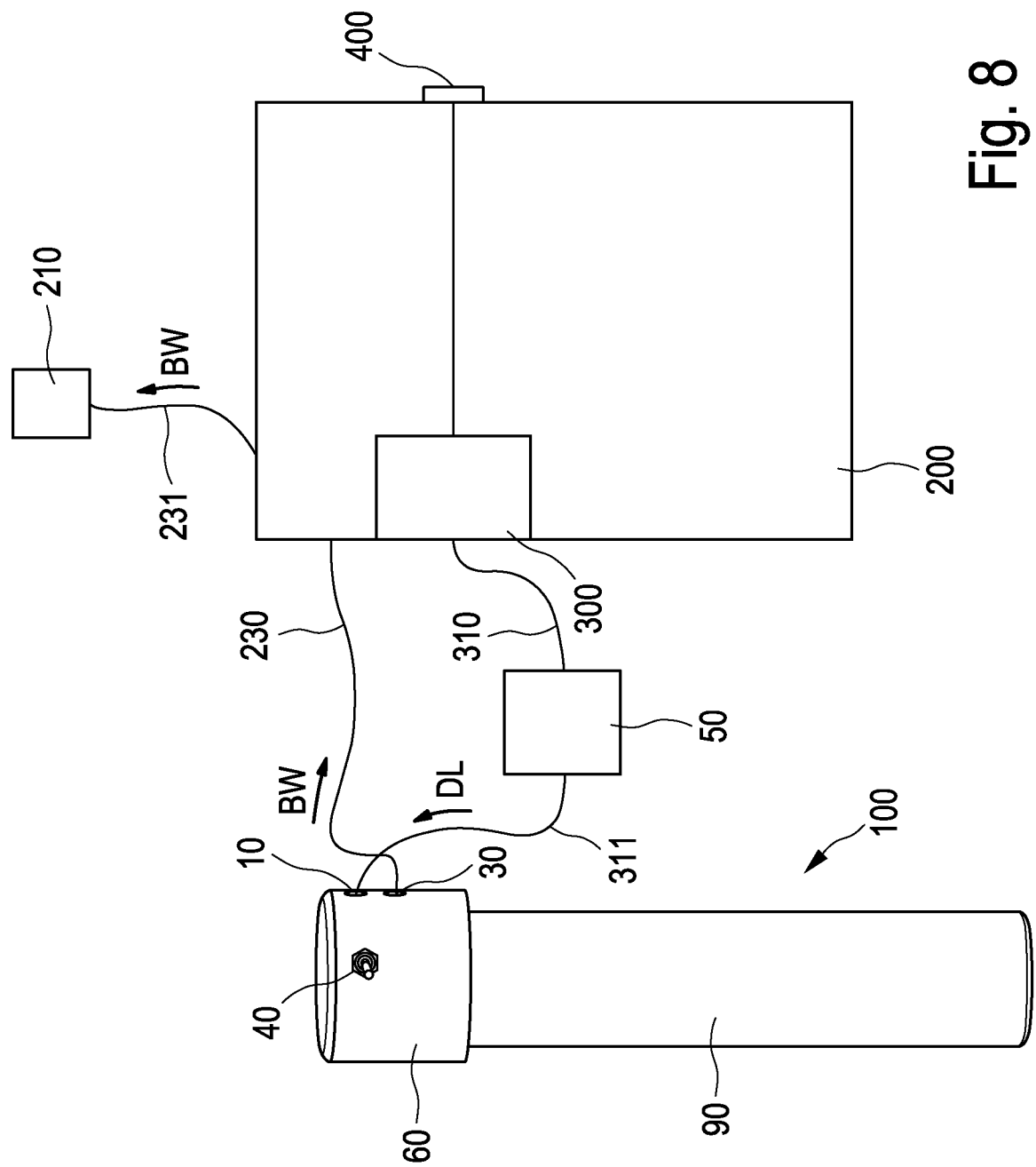
FIG. 8 shows a second embodiment example of a dental medical treatment unit having a process water supply unit.

FIG. 8 shows a process water supply unit 100 coupled to a medical treatment unit 200. In contrast to the embodiment example described with reference to FIG. 7, the sterile air filter 50 provided according to the invention is arranged in a compressed-air path between a compressed-air source 300 which is external to the process water supply unit 100 and the compressed-air inlet 10.

The sterile air filter 50 and the compressed-air source 300 are connected to one another via a compressed-air supply line 310 which, in this case, is shorter than 2 meters. The sterile air filter 50 is connected on the outlet side to the compressed-air inlet 10 via a filter line 311 which, in this case, is shorter than 2 meters. The compressed-air source 300, in this case a compressed-air connection of the medical treatment unit 200, is, for its part, supplied with pressure by a central compressed-air compressor 400.

Substantially unfiltered compressed air is supplied via the compressed-air source 300 to the sterile air filter 50, from where said compressed air travels to the compressed-air inlet 10. As already described previously, the process water BW travels from the pressurized water container 90 via the process water line 230 to the dental medical treatment unit 200. Connected to the dental medical treatment unit 200 is a rinsing head 210, into which the process water is introduced.

As an alternative to the embodiment examples shown in FIGS. 7 and 8, in which the process water supply unit 100 is arranged outside the medical treatment unit 200, the process water supply unit 100 can of course also be arranged inside a housing of a treatment unit 200.

FIG. 9 shows, by way of example, a method for operating a process supply unit according to the invention.

In a first step S1, in particular unfiltered compressed air is guided from the compressed-air source to the sterile air filter of the process water supply unit.

In a subsequent step S2, the compressed air filtered by the sterile air filter of the process water supply unit is introduced into a pressurized water container.

In a step S3, which is typically carried out within the framework of a treatment process, the pressurized water container is filled with process water, preferably containing biocide, so that the process water is dispensed via a process water connection of the process water supply device, for example to a rinsing head or drill of a dental medical treatment unit.

In an alternative or additional step S4, the pressurized water container is substantially free of process water during a cleaning phase, so that a process water path downstream of the sterile air filter or respectively the process water connection thereof is cleared by blowing by means of the compressed air filtered by the sterile air filter.

LIST OF REFERENCE NUMERALS

10 Compressed-air inlet
20 Compressed-air connection
30 Process water connection
40 Switch
50 Sterile air filter
60 Cylindrical lid part
61 Latching element on the lid part
62 Web
63 Recess
65 Bridge
70 Plate-shaped base plate
73 Recess on the base plate
75 Circumferential seal 76 Through-opening
80 Container receptacle
90 Pressurized water container
91 Latching element on the pressurized water container
95 Circumferential groove
97 Collar on the pressurized water container
100 Process water supply unit
200 Medical treatment unit
230 Process water supply line
300 Compressed-air source
310 Compressed-air supply line
320 Filter line
400 Central compressed-air compressor
BW Process water
DL Compressed air

The invention claimed is:

1. A process water supply unit for supplying a medical treatment unit with process water (BW), containing biocide, comprising:
- a pressurized water container for storing process water;
- a container receptacle for receiving the pressurized water container; and
- a cylindrical lid part accommodating the container receptacle;
- the container receptacle comprising:
  - a compressed-air inlet for connecting the process water supply unit to a compressed-air source;
  - a compressed-air connection for introducing compressed air originating from the compressed-air inlet into the pressurized water container;
  - a process water connection for dispensing the process water (BW) out from the pressurized water container by the compressed air (DL) to the medical treatment unit;
  - a sterile air filter which is integrated into a compressed-air path between the compressed-air inlet and the compressed-air connection; and
  - a plate-shaped base plate, through which the process water connection and the compressed-air connection run, wherein the plate-shaped base plate is arranged in the lid part, wherein the plate-shaped base plate is arranged completely inside the cylindrical lid part.

2. The process water supply unit according to claim 1, comprising a switch for interrupting and releasing the compressed-air path between the compressed-air inlet and the compressed-air connection.

3. The process water supply unit according to claim 1, wherein the plate-shaped base plate has a circumferential seal which seals the pressurized water container from the surroundings if the latter is fastened to the container receptacle.

4. The process water supply unit according to claim 1, comprising a sterile water filter which is arranged upstream of the process water connection.

5. The process water supply unit according to claim 1, wherein the pressurized water container has a volume between 100 ml and 5000 ml.

6. A dental medical treatment unit comprising the process water supply unit according to claim 1.

7. An ENT (ear, nose, throat) treatment unit comprising the process water supply unit according to claim 1.

* * * * *